United States Patent [19]

Gschwend et al.

[11] 4,212,808
[45] Jul. 15, 1980

[54] 2-OXIRANYL-1,4-BENZODIOXANS

[75] Inventors: Heinz W. Gschwend, New Providence; Charles F. Huebner, Chatham, both of N.J.

[73] Assignee: Ciba-Geigy Corporation, Ardsley, N.Y.

[21] Appl. No.: 18,958

[22] Filed: Mar. 9, 1979

Related U.S. Application Data

[63] Continuation-in-part of Ser. No. 940,423, Sep. 7, 1978, abandoned.

[51] Int. Cl.² ............................................. C07D 319/08
[52] U.S. Cl. .......................... 260/340.3; 260/340.5 R; 546/197; 546/199
[58] Field of Search ............................... 260/340.3

[56] References Cited

U.S. PATENT DOCUMENTS

| | | | |
|---|---|---|---|
| 2,336,093 | 12/1943 | Grün et al. .......................... | 260/340.3 |
| 2,699,438 | 1/1955 | Bock et al. ......................... | 260/340.3 X |
| 2,805,170 | 9/1957 | Bell .................................... | 260/348.15 X |
| 3,101,345 | 8/1963 | Schmidt et al. .................... | 260/340.3 |
| 3,247,155 | 4/1966 | Frank et al. ........................ | 260/348.58 |
| 3,305,564 | 2/1967 | Port et al. .......................... | 260/348.61 |
| 3,468,910 | 9/1969 | Alksnis et al. ..................... | 260/340.3 |

FOREIGN PATENT DOCUMENTS

| | | | |
|---|---|---|---|
| 771678 | 11/1967 | Canada .................................. | 260/340.3 |
| 1038332 | 8/1966 | United Kingdom ................. | 260/340.3 |
| 1038333 | 8/1966 | United Kingdom ................. | 260/340.3 |

OTHER PUBLICATIONS

Chem. Berichte 94, 901–907 (1961).

*Primary Examiner*—Ethel G. Love
*Attorney, Agent, or Firm*—Theodore O. Groeger

[57] ABSTRACT

The stereospecific process depicted, for example, by the formulae

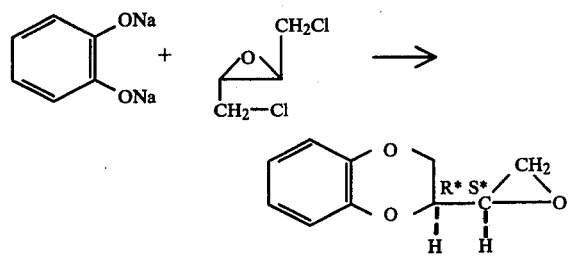

yields valuable intermediates in the manufacture of drugs.

9 Claims, No Drawings

2-OXIRANYL-1,4-BENZODIOXANS

CROSS-REFERENCE TO RELATED APPLICATION

This is a continuation-in-part of application Ser. No. 940,423 filed Sept. 7, 1978, now abandoned.

BACKGROUND OF THE INVENTION

U.S. Pat. Nos. 3,101,345; 3,312,592; 3,910,930 and 3,914,238 disclose pharmacologically active 2-(2-amino-1-hydroxyethyl)-1,4-benzodioxans, which are obtained as mixtures of diastereoisomers, separable only by cumbersome methods. According to the present invention a stereospecific process is provided, yielding intermediates for said compounds in the pure erythro or threo forms, and requiring but simple, inexpensive starting materials. Moreover, said process is especially suited for the unambiguous preparation of valuable new erythro-2-(2-aralkylamino-1-hydroxyethyl)-1,4-benzodioxans.

SUMMARY OF THE DISCLOSURE

The present invention concerns and has for its object the provision of a new stereospecific process for the preparation of 2-oxiranyl-1,4-benzodioxans corresponding to Formula I

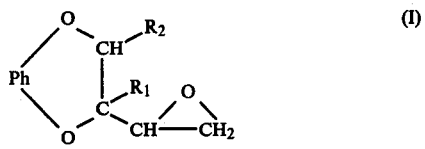

wherein Ph is unsubstituted 1,2-phenylene or 1,2-phenylene substituted by one to three identical or different members selected from lower alkyl, lower alkoxy, lower alkylenedioxy, benzyloxy, halogeno, trifluoromethyl or nitro; and each of $R_1$ and $R_2$ is hydrogen or lower alkyl, which compounds are valuable intermediates for therapeutically useful products, e.g. β-adrenergic blocking or antihypertensive agents.

Said stereospecific process comprises condensing compounds of Formulae II and III:

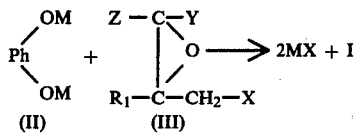

wherein M is one equivalent of a strong base, X is a reactively esterified hydroxy group and one of Y and Z is $R_2$ and the other is $CH_2X$, i.e. the oxiran-reagent III may be either in the trans- or cis-form, thus yielding the erythro-compounds of Formula I, or the threo-compounds respectively.

The conversion of said compounds of Formula I into therapeutically useful products is disclosed in said patents, but without reference to a stereochemically single entity, which surprisingly exhibits all the pharmacological activity.

DESCRIPTION OF THE PREFERRED EMBODIMENTS

The 1,2-phenylene group Ph is preferably unsubstituted or monosubstituted, and its substituents are illustrated by the following groups; lower alkyl, e.g. methyl, ethyl, n- or i-propyl or -butyl; lower alkoxy, e.g. methoxy, ethoxy, n- or i-propoxy or -butoxy; lower alkylenedioxy, e.g. methylenedioxy, 1,1- or 1,2-ethylenedioxy; benzyloxy; halogeno, e.g. fluoro, chloro or bromo; trifluoromethyl; or nitro.

Each of $R_1$ and $R_2$ if preferably hydrogen, but also lower alkyl advantageously methyl, or another of those mentioned above.

The symbol M represents preferably an alkali metal atom, especially sodium, but also lithium or potassium; or the ion of a strong tertiary or quaternary nitrogen base, such as 1,5-diazabicyclo[4,3,0]non-2-ene, 1,5-diazabicyclo[5,4,0]undec-5-ene or trimethylbenzylammonium hydroxide.

A reactively esterified hydroxy group X is preferably a halogen atom, especially chloro, but also bromo or iodo; or an aliphatic or aromatic sulfonyloxy group, such as mesyloxy, benzenesulfonyloxy, tosyloxy or brosyloxy.

The above-mentioned condensation step is carried out in the presence of diluents, preferably such as are inert to the reagents and are solvents thereof, such as lower alkylformamides or sulfoxides, e.g. dimethylformamide or -sulfoxide, of catalysts, condensing agents and/or inert atmospheres, at low temperatures, room temperature or elevated temperatures, preferably between about 50 and about 70° C., at atmospheric or superatmospheric pressure. Said condensation step may also be carried out in an aqueous medium, which advantageously contains a phase-transfer agent, such as a tetra-lower alkylammonium hydroxide, e.g. tetrabutylammonium hydroxide, or crown-ethers, and/or lower alkanols, e.g. methanol, ethanol or isopropanol.

The starting material is known, or if new, may be prepared according to standard methods. Thus, for example, the salts of Formula II may be prepared from the corresponding catechols and strong bases, such as alkali metal hydroxides, lower alkoxides or hydrides; or lower trialkylbenzylammonium hydroxides.

The oxiranes of Formula III are conventionally obtained from corresponding esters of cis- or trans-butenediols, by epoxidation with aliphatic or preferably aromatic peracids, such as peracetic, persuccinic, perbenzoic, m-chloroperbenzoic or monoperpthalic acid, and any excess thereof should be destroyed after the olefin has been consumed, e.g. with sodium sulfite. Said oxiranes may also be prepared by catalytic oxidation with air or oxygen in the vapor phase, e.g. over silver, platinum or palladium catalysts.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or they are used in the form of optically pure antipodes. Mainly such starting materials should be used in said reaction, which lead to the formation of those compounds indicated below as being especially valuable, e.g. for those mentioned in said patents.

The compounds of Formula I, so obtained, are preferably those wherein Ph is 1,2-phenylene unsubstituted, mono-or disubstituted by alkyl or alkoxy with 1–4 carbons, alkylenedioxy with 1 or 2 carbon atoms, benzyloxy, fluoro, chloro, bromo, trifluoromethyl or nitro, and each of $R_1$ and $R_2$ is hydrogen or methyl.

More preferred are compounds of Formula I, wherein Ph is 1,2-phenylene unsubstituted, mono- or disubstituted by methyl, methoxy, methylenedioxy, benzyloxy, fluoro, chloro, trifluoromethyl or nitro, and each or $R_1$ and $R_2$ is hydrogen.

Most preferred is the compound of Formula I wherein Ph is 1,2-phenylene, 4,5- or 3,6-dimethoxy-1,2-phenylene and each of $R_1$ and $R_2$ is hydrogen.

The respective starting material of Formulae II and III correspond to said subgeneric compounds of Formula I, and the preferred compounds of Formula III are the trans-isomers, i.e. those wherein $Y=R_2$ and $Z=CH_2-X$.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the solution of 1.32 g of catechol in 15 ml of dimethylsulfoxide 0.8 g of sodium hydroxide pellets are added while stirring under nitrogen at 55°. After about 4 hours the dark green solution is combined with 1.5 g of trans-2,3-bis-chloromethyloxirane and stirring is continued for 4 hours at 55°–60°. After cooling to room temperature, the mixture is diluted with 100 ml of water and extracted with diethyl ether. The extract is washed with aqueous sodium hydroxide and saturated aqueous sodium chloride, dried and evaporated, to yield 1.6 g of a light yellow oil. It is chromatographed on silica gel, and eluated with chloroform, to yield after evaporation 0.9 g of a colorless oil which solidifies on standing. It is crystallized from diethyl ether, to yield the d,l-erythro- or 2-[(2S*)-oxiranyl]-1,4-(2R*)-benzodioxan of the formula

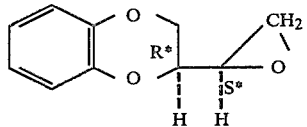

melting at 51°–52°.

The starting material is prepared as follows: To the stirred solution of 0.2 molar m-chloro-perbenzoic acid in 275 ml of methylene chloride is added the solution of 25 g of trans-1,4-dichloro-2-butene in 50 ml of methylene chloride. The mixture is stirred at room temperature for 4 days, filtered and the filtrate stirred for 30 minutes with 100 ml of 10% aqueous sodium sulfite. The organic layer is separated, washed with cold 12% aqueous sodium hydroxide and water, dried and evaporated to yield the trans-2,3-bis-chloromethyloxirane boiling at 85°–88°/25 mmHg.

EXAMPLE 2

To the solution of 1.32 g of catechol in 60 ml of dimethylformamide is added 0.96 g of a 50% suspension of sodium hydride in mineral oil while stirring under nitrogen at 50°–55°. After 30 minutes the solution of 1.5 g of cis-2,3-bis-chloromethyloxirane in 5 ml of dimethylformamide is added and the mixture heated and stirred for 2½ hours longer. It is cooled and worked up as described in Example 1, to yield the d,l-threo- or 2-[(2R*)-2-oxiranyl]-1,4-(2R*)-benzodioxan of the formula

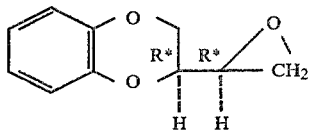

melting at 45°.

EXAMPLE 3

The mixture of 1.7 g of cis-2,3-bis-chloromethyloxirane, 1.1 g of catechol and 2 ml of isopropanol is heated to 65° and the solution of 0.8 g of sodium hydroxide in 2 ml of water is added dropwise while stirring. The mixture is heated to 85° for 60 minutes, cooled and diluted with benzene. It is washed with water, dried and evaporated, to yield a mixture comprising 48% starting oxirane; 40% desired d,l-threo-2-oxiranyl-benzodioxane and 10% of 2-chloromethyl-3-hydroxymethyl-benzodioxane (by mass-spectroscopy). It is separated by bulb to bulb-distillation and the fraction boiling at 120°/0.2 mmHg collected, to yield said threo-compound.

The starting material is prepared in the exact analogous manner as described in Example 1, by merely replacing the trans-1,4-dichloro-2-butene by the same amount of the cis-isomer.

EXAMPLE 4

The mixture of 3 g of d,l-erythro-2-oxiranyl-1,4-benzodioxan, 1.9 g of 4-hydroxy-4-phenylpiperidine and 20 ml of isopropanol is refluxed for 7 hours. After cooling to room temperature 0.7 ml of methanesulfonic acid are added while stirring and the mixture is allowed stand in the refrigerator overnight, to yield the d,l-erythro-2-[2-(4-hydroxy-4-phenylpiperidino)-1-hydroxyethyl]-1,4-benzodioxan methanesulfonate, melting after recrystallization from aqueous isopropanol-diethyl ether at 212°–213°.

1 g thereof is suspended in 20 ml of water, the mixture made basic with aqueous sodium hydroxide and extracted with methylene chloride. The extract is dried, evaporated and the residue recrystallized from isopropanol, to yield the corresponding free base melting at 118°. It is identical with that disclosed in U.S. Pat. No. 3,914,238.

EXAMPLE 5

The mixture of 2.5 g of d,l-erythro-2-oxiranyl-1,4-benzodioxan, 1.7 g of 2-(2-oxo-1-benzimidazoyl)-piperidine and 15 ml of isopropanol is refluxed for 4 hours and concentrated to a small volume. The concentrate is diluted with benzene and extracted with 5% hydrochloric acid. The extract is allowed to stand in the cold, the gummy precipitate formed filtered off and triturated with aqueous ammonia and chloroform. The organic solution is separated, dried, evaporated and the residue recrystallized from ethyl acetate, whereby the d,l-erythro-2-[2-(4-(2-oxo-1-benzimidazolyl)-piperidino)-1-hydroxyethyl]-1,4-benzodioxan is obtained, melting at 188°–190°; it is identical with that of German Pat. No. 2,400,094.

The analogously obtained d,l-threo-compound melts at 110°–115°.

EXAMPLE 6

To the solution of 1,095 g of catechol and 1,390 g of trans-2,3-bis-chloromethyloxiran in 9,870 ml of dimethylsulfoxide 711 g of sodium hydroxide pellets are added while stirring under nitrogen at 8°. Stirring is continued overnight at room temperature, whereupon 49,000 ml of water are quickly added. The mixture is extracted with diethyl ether, the extract washed with water, dried and evaporated. The residual oil is distilled and the fraction boiling at 76°–102°/0.05 mmHg collected to yield the d,l-erythro-or 2-[(2S*)-oxiranyl]-1,4-(2R*)-benzodioxan melting at 46°–48°; it is identical (but somewhat less pure) with that obtained according to Example 1.

The starting material is prepared as follows: To the stirred solution of 7,250 g of m-chloro-perbenzoic acid in 4,500 ml chloroform is added 4,125 g of trans-1,4-dichloro-2-butene during 15 minutes while stirring under nitrogen at room temperature. After 1 hour the mixture is refluxed for 48 hours and stirred at 10° C. for 1 hour. It is filtered, the residue washed twice with 4,000 ml of chloroform, and the combined filtrates are washed with 0.5 N of aqueous sodium hydroxide and water. They are dried, evaporated, the residue distilled and the fraction boiling at 87°–89°/20 mmHg collected, to yield the trans-2,3-bis-chloromethyloxiran.

Analogously the d,l-threo- or 2-[(2R*)-oxiranyl]-1,4-(2R*)-benzodioxan is obtained from the cis-2,3-bis-chloromethyloxiran, melting at 45°; it is identical with that of Example 2.

What is claimed is:

1. Process for the stereospecific preparation of compounds of the formula

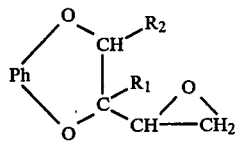

wherein Ph is unsubstituted 1,2-phenylene or 1,2-phenylene substituted by one to three identical or different members selected from lower alkyl, lower alkoxy, lower alkylenedioxy, benzyloxy, halogeno, trifluoromethyl or nitro, and each of $R_1$ and $R_2$ is hydrogen or lower alkyl, which comprises condensing compounds of the formulae

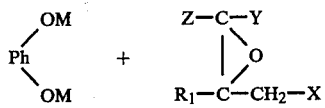

wherein M is one equivalent of a strong base, X is a reactively esterified hydroxy group and one of Y and Z is $R_2$ and the other is $CH_2X$.

2. Process according to claim 1 wherein reactants are selected in which M is an alkali metal or lower trialkylbenzylammonium.

3. Process according to claim 1, wherein reactants are selected in which X is halogeno or aliphatic or aromatic sulfonyloxy.

4. Process according to claim 1, wherein reactants are selected in which M is sodium.

5. Process according to claim 1, wherein reactants are selected in which X is chloro.

6. Process according to claim 1, wherein reactants are selected in which Ph is 1,2-phenylene unsubstituted, mono- or disubstituted by alkyl or alkoxy with 1–4 carbons, alkylenedioxy with 1 or 2 carbons, benzyloxy, fluoro, chloro, bromo, trifluoromethyl or nitro, and each of $R_1$ and $R_2$ is hydrogen or methyl.

7. Process according to claim 1, wherein reactants are selected in which Ph is 1,2-phenylene unsubstituted, mono- or disubstituted by methyl, methoxy, methylenedioxy, benzyloxy, fluoro, chloro, trifluoromethyl or nitro, and each of $R_1$ and $R_2$ is hydrogen.

8. Process according to claim 1, wherein reactants are selected in which Ph is 1,2-phenylene, 4,5-dimethoxy- or 3,6-dimethoxy-1,2-phenylene, and each of $R_1$ and $R_2$ is hydrogen.

9. Process according to claim 1, wherein the condensation is carried out in a lower alkylated formamide or sulfoxide between about 50 and about 70° C.

* * * * *